United States Patent [19]
Kristinsson

[11] Patent Number: 5,885,509
[45] Date of Patent: Mar. 23, 1999

[54] APPARATUS AND PROCESS FOR FORMING PROSTHETIC SOCKET

[75] Inventor: Ossur Kristinsson, Reykjavik, Iceland

[73] Assignee: Ossur HF, Reykjavik, Iceland

[21] Appl. No.: 958,665

[22] Filed: Oct. 28, 1997

Related U.S. Application Data

[60] Provisional application No. 60/030,875 Oct. 30, 1996.
[51] Int. Cl.[6] .............................. A61F 2/62; B28B 21/42; B29C 43/12
[52] U.S. Cl. .................................. 264/314; 264/DIG. 30; 425/2; 425/389; 623/33; 623/901
[58] Field of Search ........................ 425/2, 389; 264/314, 264/DIG. 30; 623/33, 901

[56] References Cited

U.S. PATENT DOCUMENTS

| | | | |
|---|---|---|---|
| 980,457 | 1/1911 | Toles | 623/34 |
| 2,424,278 | 7/1947 | Kunkel | 264/222 |
| 3,128,322 | 4/1964 | Young | 264/314 |
| 3,513,059 | 5/1970 | Prohaska | 156/446 |
| 4,475,976 | 10/1984 | Mittelstadt et al. | 264/314 |
| 4,923,474 | 5/1990 | Klasson et al. | 623/33 |
| 5,226,918 | 7/1993 | Silagy et al. | 623/33 |
| 5,503,543 | 4/1996 | Laghi | 425/2 |
| 5,718,925 | 2/1998 | Kristinsson et al. | 425/2 |

FOREIGN PATENT DOCUMENTS

| | | | |
|---|---|---|---|
| 1018-633-A | 5/1983 | Russian Federation . | |
| 1109-150-A | 8/1984 | Russian Federation | 623/33 |
| 1195-996-A | 12/1985 | Russian Federation | 623/33 |
| 1586-703-A | 8/1990 | Russian Federation | 623/901 |
| 2 149 309 | 6/1985 | United Kingdom | 623/901 |

OTHER PUBLICATIONS

H. Gardner, "A Pneumatic System for Below–Knee Stump Casting", *Prosthetic International*, vol. 3, pp. 12–14 (1968).
Ossur hf undated Brochure for ICECAST Pressurized Casting Instrument, 9 pages, No Date.

*Primary Examiner*—Robert Davis
*Attorney, Agent, or Firm*—Bacon & Thomas, PLLC

[57] ABSTRACT

A prosthesis socket casting device includes a base member on which an elongated annular molding bladder is mounted, the bladder peripherally enclosing a generally centrally located casting area and extendable when inflated from the forward side of the base. The bladder is formed of a pliable, air impermeable, relatively non-stretchable sheet material enclosing, in cooperation with the base, an air chamber peripherally surrounding the casting area. The casting area includes an open residual limb receiving end and extends from such end to the base, and an inflation system for the bladder is provided. The casting device may be used in conjunction with a prosthesis suction socket that includes a tension member at its distal end connectable to the base member during a casting procedure. Moldable and settable prosthesis socket or other moldable casting material is placed over the suction socket and is compression molded by the inflated bladder while the casting material cures. During the compression casting procedure, a tension force resulting from the bladder inflation pressure may be applied to the distal end of the suction socket to elongate and distend the distal area of the residual limb against which the casting material is formed under pressure. The bladder is rollable relative to the base member to provide ready access to the tension member connector carried by the base member.

38 Claims, 6 Drawing Sheets

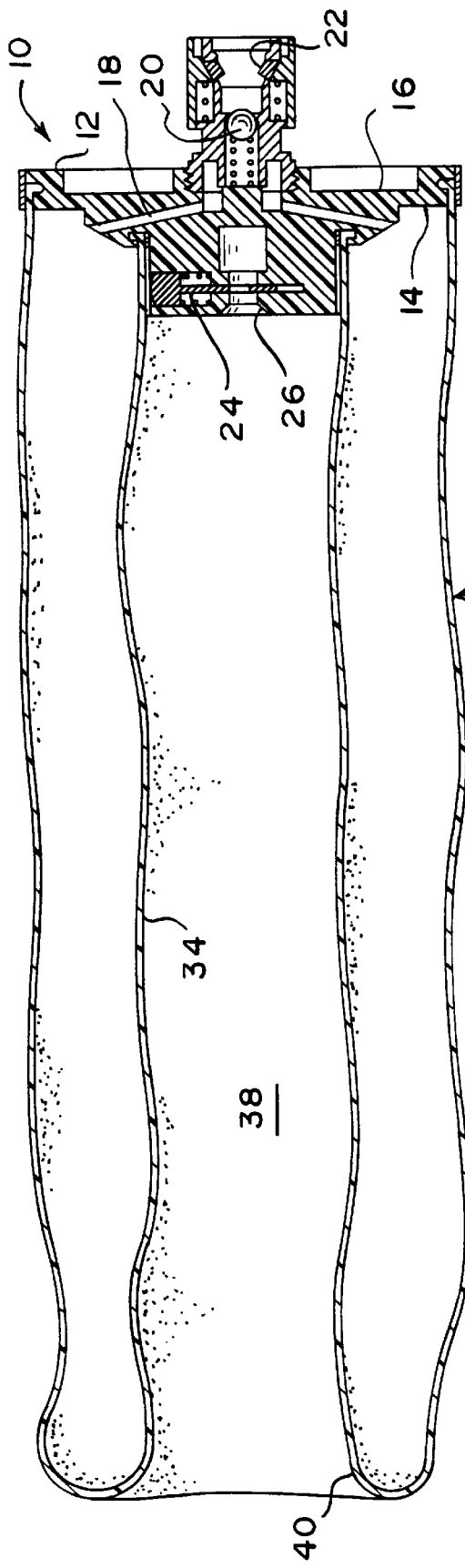
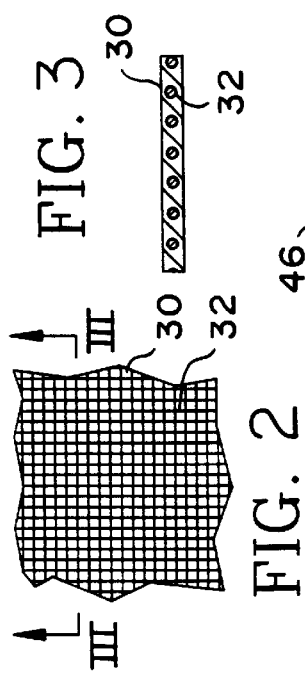
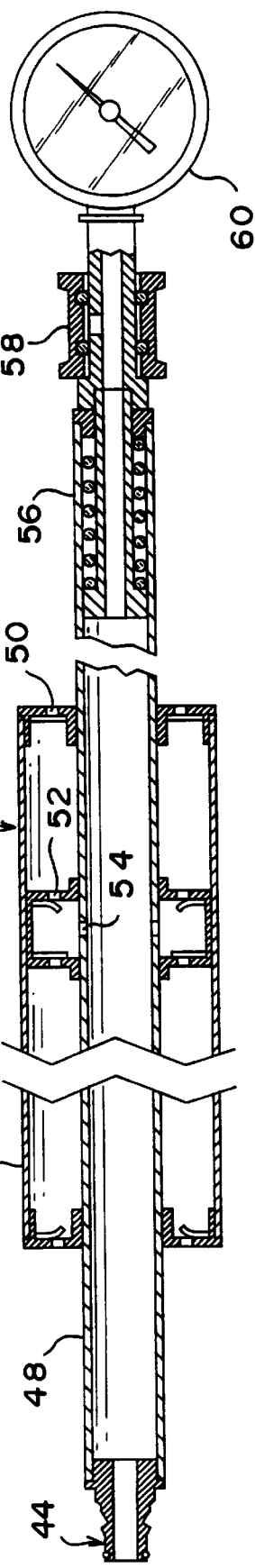
FIG. 1
FIG. 3
FIG. 2
FIG. 4

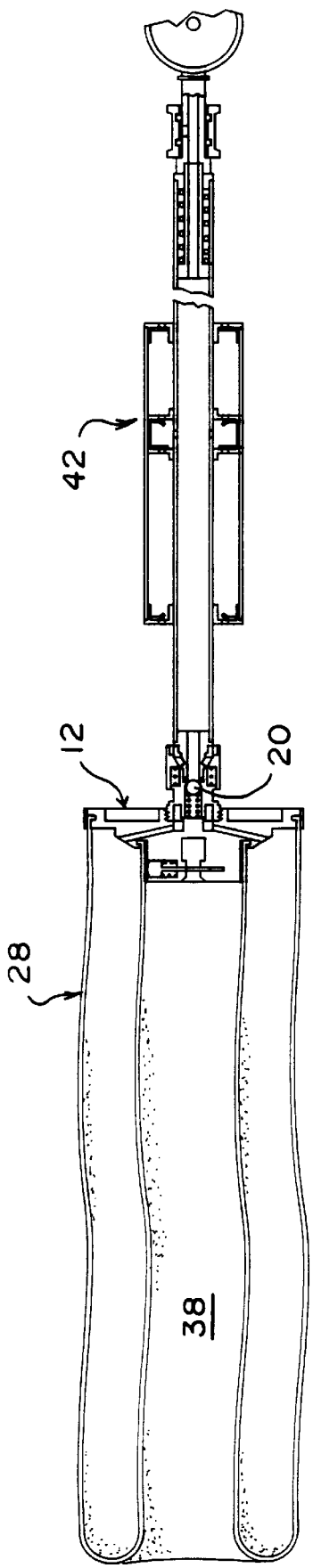
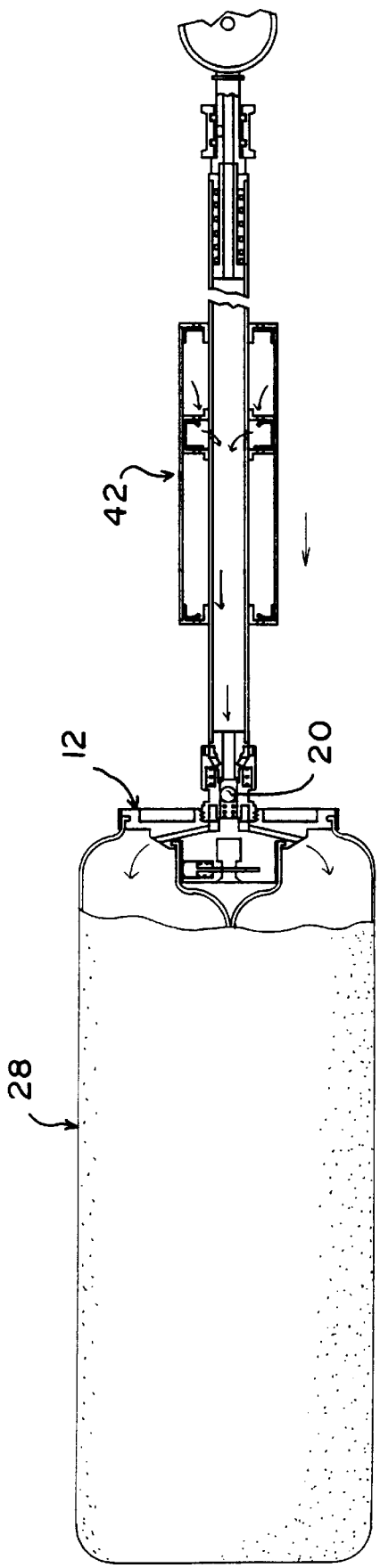

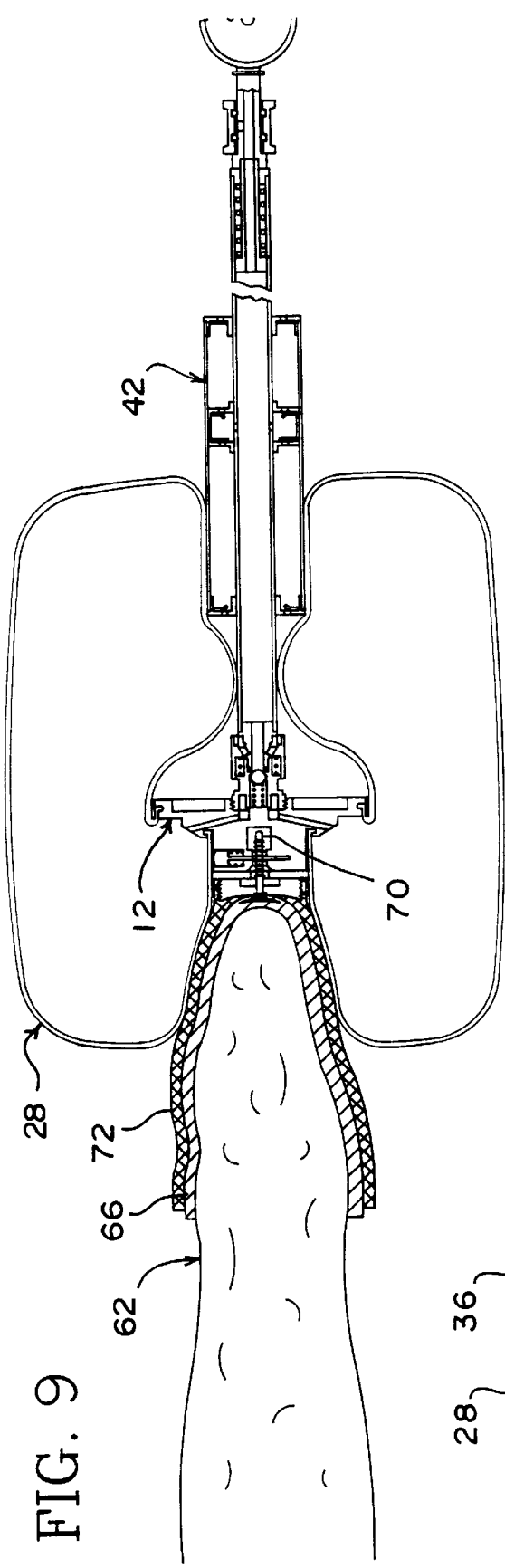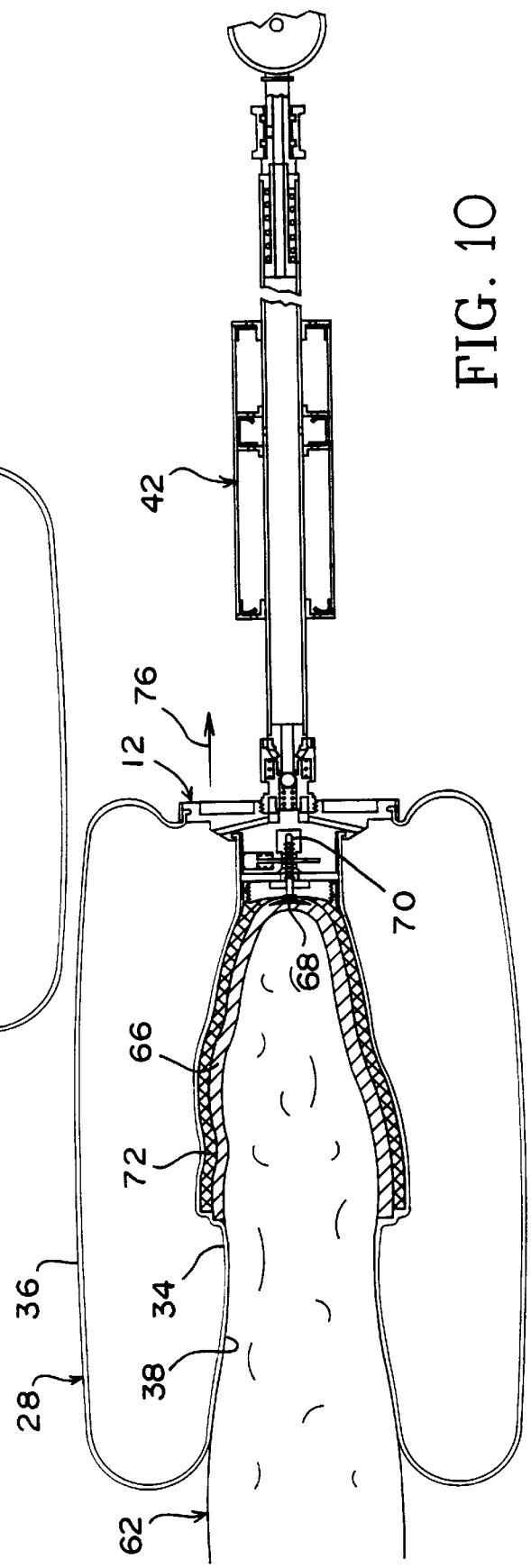

APPARATUS AND PROCESS FOR FORMING PROSTHETIC SOCKET

CROSS REFERENCE TO RELATED APPLICATION

Applicant(s) named herein claim benefit of U.S. Provisional Application No. 60/030,875 filed Oct. 30, 1996, under 35 U.S.C. §119(e) naming an Applicant named herein as an inventor.

BACKGROUND OF THE INVENTION

1. Field of the Invention

This invention relates to an apparatus and method for forming or casting prosthesis or prosthetic sockets on residual limbs.

2. Background of Related Art

Residual limb sockets are formed in accordance with the prior art using various apparatus and methods, including molding thermosetting, thermoforming or other resinous materials to obtain a relatively rigid socket for connecting a residual limb to a prosthesis device without discomfort to the user. Such molded sockets without and with reinforcements are exemplified in U.S. Pat. Nos. 5,163,965, granted Nov. 17, 1992, to Rasmusson and Fischel; and 5,263,990, granted Nov. 23, 1993, to Handal.

Prior art techniques include molding sockets of resinous materials using a male or positive mold of the residual limb that is formed from a plaster of paris female or negative casting sleeve that has been formed by molding the sleeve directly on the residual limb. It is also known to form the definitive socket using a pressure casting system exemplified by the ICECAST® system made by Ossur HF of Reykjavik, Iceland. The positive mold is then adjusted or "rectified" in accordance with well known techniques to provide relief for sensitive areas of the residual limb and to obtain a correctly sized socket that will properly fit the residual limb.

Other procedures for molding interim or definitive sockets have been described in the prior art, including a procedure whereby SCOTCHCAST® tape made by 3M Company of Minneapolis, Minn. has been utilized to produce an interim prosthesis socket for below-knee amputees.

Existing apparatus for forming prosthetic sockets on residual limbs tend to be bulky and somewhat complex. It is desirable to provide a simplified and compact prosthesis socket casting or forming system that not only facilitates pressure casting or molding of prosthesis socket or molding material directly on the distal end area of a residual limb but which also enables tension to be applied to the distal end area of the residual limb during the casting process to produce a better fitting socket.

BRIEF SUMMARY OF THE INVENTION

The present invention is a prosthesis socket casting device formed of a base on which is mounted an elongated annular molding bladder that peripherally encloses a generally centrally located casting area extendable from the base over a length of the bladder. Preferably, the bladder comprises a pliable, air impermeable, relatively non-stretchable sheet material enclosing, in cooperation with the base member, an air chamber peripherally surrounding the casting area when the bladder extends away from the forward side of the base and is at least partially inflated to tension the bladder material. The base preferably carries a tension member connector for engaging a tension member associated with a suction socket previously mounted on the distal end area of a residual limb on which a prosthesis socket is to be cast. The base also includes an air passage in communication with the bladder air chamber and a valve in the air passage arranged to control flow of air through the passage.

A moldable and settable prosthesis socket sleeve material (which may be any suitable moldable and settable molding material, including plaster or paris) is positioned over a suction sleeve having a tension member or guide pin extending through the prosthesis socket material in engagement with the tension connector carried by the base or simply extending into the base as a centering guide. The prosthesis sleeve optionally includes a prosthetic device coupler at its distal end that may constitute part of the prosthesis sleeve and ultimately the prosthesis socket. The prosthesis socket material is castable and moldable over the residual limb but is not cured when it is first placed over the suction socket and limb.

Extension over and inflation of the bladder on the residual limb distal area on which the suction socket and moldable prosthesis sleeve material have been previously placed enables compression of the residual limb distal area including the prosthesis sleeve material while the prosthesis sleeve material undergoes curing and setting to a relatively rigid, structural form. However, due to the geometry of the bladder and the configuration of the distal area of the residual limb, the suction socket and the prosthesis socket casting material, a resultant tractive force between the base member and the suction sleeve is generated and transmitted to a tension member when used and when the bladder is inflated so as to compress the residual limb distal end area with the suction socket and the prosthesis socket casting material. This tractive force results in elongation of the residual limb distal area during compression thereof by the bladder and is proportional to the inflation pressure of the bladder and other variables. The combination of compressive and tension forces on the residual limb distal area produces a prosthesis socket from the socket material after curing of the latter that is comfortable to the user without further substantial adjustment of the socket. The socket material may include appropriate fabric inner and outer covering to render the socket comfortable when worn and for cosmetic purposes.

The invention includes a hand pump that may be attached to the base member for pressurizing the bladder wherein both the base member and the hand pump may be connected together by a quick engage/release coupling and fitting that opens a normally closed check valve in the air passage communicating with the interior of the bladder so that the bladder may be supplied with pressurized air from the pump when the pump and base member are connected together. The valve otherwise blocks egress of air from the bladder.

The bladder may be formed of a continuous tubular element folded inside out over itself to produce two tubular sections, one inside the other, the free ends of which are connected in sealing relationship to the base member. An air chamber is thus produced between the inner and outer tubular sections connected to the base member and the air chamber is in communication with an air passage in the base member.

The bladder may be formed of a silicone rubber material in which is embedded a fabric or fiber reinforcement that renders the fabric relatively non-extendable while leaving it highly compliant and pliable so that it follows the contours of a residual limb in the casting area located within the inner tubular section of the bladder.

The bladder may be conveniently rolled forward and backward relative to the base member when partially inflated so as to expose the forward side of the base member to a tension member that may be associated with the suction socket. A tension member connector and a release mechanism, if used, is also accessible from the forward side of the base member when the bladder is rolled rearwardly relative to the base member. Rolling the bladder forwardly over the distal end area of a residual limb on which a suction socket and prosthesis material have been placed envelops the prosthesis material and urges the material into close conformity with the residual limb distal end area, particularly after the bladder has been inflated up to a selected pressure to cause compression forming or casting of the prosthesis socket material during its curing process. As noted previously, this compression force also produces a net tension or tractive force exerted on the tension member that elongates and tensions the distal area of the residual limb during the compressive casting procedure to produce a better fitting prosthesis socket from the curing socket sleeve material.

Optionally, the tension member and tension connector member may be altered so that simple compression casting may be carried out without tension or tractive force applied to the suction socket.

The prosthesis sleeve molding material preferably is constituted of a matrix of reinforcement impregnated with a water curable resinous material that is prepared as a preformed rolled sleeve that may be readily donned over the residual limb distal area. Various resin-reinforcement combinations may be utilized and a specific preferred material is described in more detail below.

BRIEF DESCRIPTION OF THE DRAWINGS

FIG. 1 is an elevation section view showing a prosthesis socket casting device constructed in accordance with the present invention and in particular the annular molding bladder carried by a base member that includes in this embodiment a releasable tension member connector and an air conduit for admitting and releasing air into and from an air chamber in the molding bladder;

FIG. 2 shows a detail of the silicone bladder material illustrating reinforcement fibers used in the material;

FIG. 3 is a section view taken along line III—III of FIG. 2;

FIG. 4 shows an air pump usable with the molding bladder assembly for inflating the bladder and also for providing a tension sensing and reading device and a pressure gauge associated with the pump;

FIGS. 5 and 6 show the molding bladder during inflation of the bladder;

FIGS. 9 and 10 show the bladder progressively rolled forwardly relative to the base over the silicone sleeve and moldable prosthesis material with the bladder in partially inflated condition;

DETAILED DESCRIPTION OF PREFERRED EMBODIMENT(S)

Figure 7:
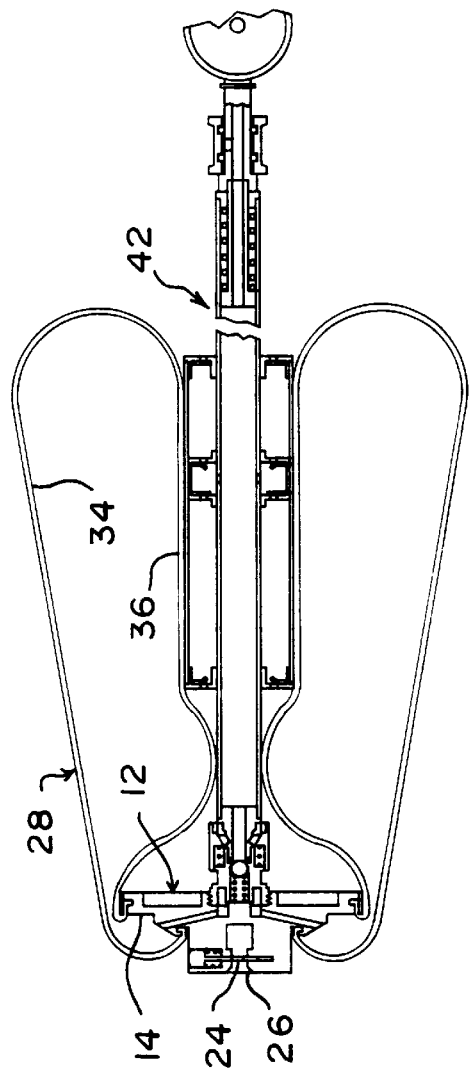
FIG. 7 shows the bladder rolled rearwardly from the base with the pump connected to the base.

With reference to the drawings, a prosthesis socket casting device 10 in accordance with a preferred form of the invention includes a base member 12 having a forward side 14 and a rear side 16. Base member 12 also preferably includes an air passage 18 that extends rearwardly from the rear side 16 but which is normally closed by a spring-biased ball type check valve 20 that maintains the air passage closed to egress of air outwardly through the rear side 16 of base member 12. An air passage quick engage/release coupling 22 enables fitting of a pump member (to be described below) to the base member 12 for opening check valve 20 and admitting selectively pressurized air into conduit 18.

Base member 12 also includes a releasable tension member connector 24 that constitutes a spring-biased apertured plate that engages a pin-like tension member (to be described later) during pressurized casting of a prosthesis socket on the distal area of a residual limb. An aperture 26 on the forward side of base member 12 provides access to the tension member connector 24 from a casting chamber defined by an inflatable annular molding bladder 28 connected to the forward side of the base member 12.

Molding bladder 28 is preferably formed of silicone rubber reinforced by a web or strands of material that is or are relatively non-extensible as compared with the rubber material of the bladder. FIGS. 2 and 3 represent the bladder material 30 formed of a sheet of pliable and compliant silicone rubber, for example, or any other pliable and body member conforming material, with a web or strands of reinforcement material 32 embedded in the silicon rubber to render the bladder material relatively inextensible in both radial and longitudinal directions. Essentially, the bladder material is configured and formed so as to provide an inflatable bladder that will not distend beyond a fixed total volume that will be defined by the bladder material and, in accordance with the preferred embodiment, the base 12.

In the preferred embodiment, the bladder material 30 is formed of a singular tube of sheet-like bladder material folded inside out over itself so as to form a continuous tubular bladder having inner and outer tube sections as illustrated, with the free ends of the tubular member sealingly anchored to the base member 12. In accordance with the preferred embodiment, the inner section 34 of the folded over tubular element may have a smaller end diameter than the outer section 36 and both ends may be secured to the forward side of the base member 12. Alternatively, the free ends of the tubular member having sections 34, 36 may be configured so as to sealingly connect to the base member 12 in any appropriate manner. A preferred embodiment of securing the free ends of the tubular sections 34, 36 to the base member 12 may be seen in FIG. 12, to be discussed in more detail below.

Figure 13:
FIG. 13 shows an alternate form of the bladder.

Alternatively, the tubular sections 34, 36 may be formed of inner and outer tubular elements formed of similar pliant but relatively inextensible material wherein the inner ends of the tubular elements are sealingly connected to the base 12 and the outer ends of the tubular elements are sealingly connected together at their ends 35 opposite the base 12 as shown in FIG. 13. Clearly, any suitable arrangement for providing an inflatable bladder that will define a generally central casting area to be described momentarily may be used for the bladder element 28. The essential characteristic of the bladder 28 is that it is formed of a material that will not itself distend substantially when tensioned, yet the bladder will be fully compliant when inflated to envelop a residual limb located within the inner tube section 34, which is intended to constitute a generally central prosthetic socket casting area 38.

The casting area 38 within the inner tube section 34 extends from the aperture 26 located on the forward side of the base 12 forwardly to an open, residual limb receiving opening 40 that may be moved relative to the base 12 in a manner to be discussed below in connection with FIGS. 7–10.

The cross-sectional area and the total volume of the casting area 38 when empty is intended to be smaller than the cross-sectional area and volume of a residual limb distal area, suction socket and prosthesis socket material placed within the casting area during casting of a prosthesis socket, which will be described momentarily. That is, when the bladder 28 is inflated to sufficient pressure to place the bladder material in tension, the total volume of the casting area 38 will be smaller than the volume of a residual limb distal area, a suction socket placed on the residual limb distal area and prosthesis socket material to be molded in place on the residual limb distal area.

Preferably, a hand pump 42 illustrated in FIG. 4 may be provided to selectively pressurize the bladder 28. The pump 42 includes a pump quick engage/release fitting 44 at its forward end for mating with the air passage quick engage/release coupling 22 associated with the air passage 18 in base member 12. Such quick engage/release couplings and fittings are well-known to those skilled in the art and do not constitute per se a part of the present invention. Any appropriate quick engage/release coupling or fitting may be used to achieve the function of detachably coupling the pump 42 to the base member 12 for selectively supplying pressurized air to the air passage 18 and the bladder 28.

Alternatively, of course, any suitable air supply air passage or pump could be used, for example a direct air supply fitting (not shown) on the bladder itself, similar to fittings used on pneumatic tires, inflated balls and toys.

The pump 42 may include a hand movable double acting piston 46 slidable along an elongated cylinder 48 so as to deliver pressurized air from outside piston 46 via conduits 50, 52, 54 to the interior of cylinder 48 and ultimately to air passage 18 via check valve 20. In accordance with known quick engage/release couplings, the fitting 44 of pump 42 will be arranged to displace normally closed ball check valve 20 to an open position to enable pressurized air to be introduced into the bladder 28 upon actuation of the pump 42. However, the pump 42 preferably will hold air pressure that is within the bladder air chamber.

Pump 42 may include a tension indicator at 56, a pressure release valve 58 and a pressure indicator 60 for indicating static pressure in the bladder 28 when pump 42 is connected to base 12. The pressure release valve 58, obviously, is provided to controllably relieve air pressure from within bladder 28 in a selectable manner.

FIG. 5 shows the pump 42 connected to base 12 with the bladder 28 in relatively relaxed condition while extending forwardly from the forward side of the base 12. Manipulation of the pump 42 enables inflation of the bladder 28 as shown in FIG. 6, where the check valve 20 is shown in the open position and pressurized air from pump 42 is delivered to the interior of bladder 28 via the air passage 18. It will be observed that the centrally located casting area 38 within the interior of the bladder 28 is relatively small compared with the total size of the bladder and may be configured in any desirable shape or form to accommodate a casting operation to be described below.

Figure 8:
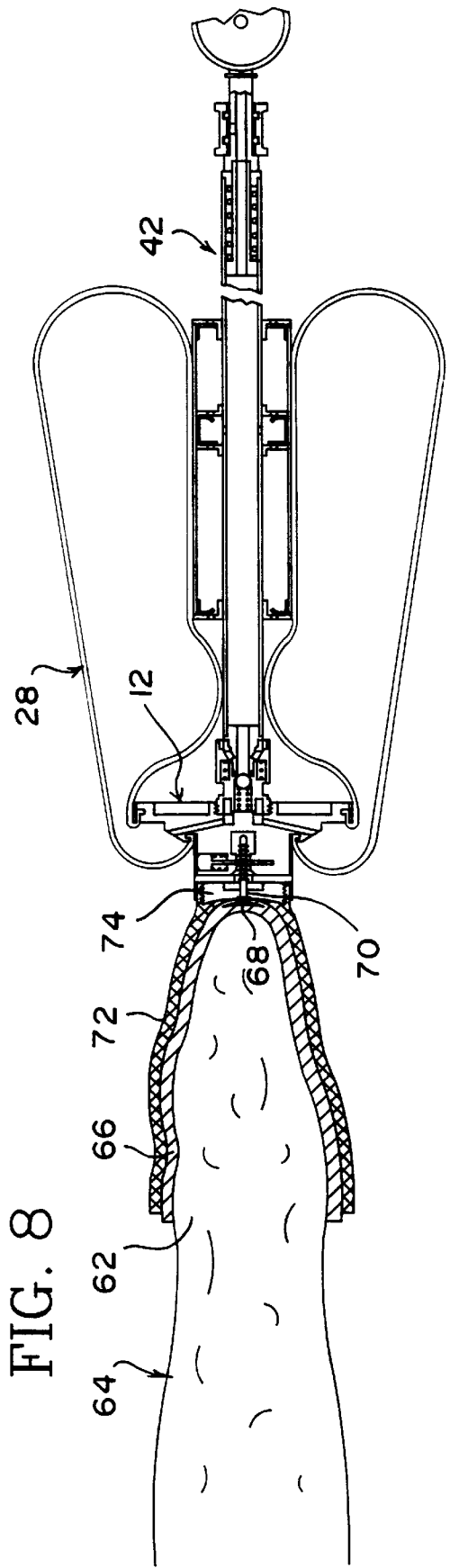
FIG. 8 shows a suction socket donned on a residual limb with a tension connector extending from the distal end of the suction socket connected to the base, and a moldable and settable prosthesis material with a prosthesis coupler mounted over the suction sleeve between the suction sleeve and the base.

As illustrated in FIGS. 7 and 8, to enable access to aperture 26 and tension member connector 24 located on the forward side 14 of base 12, the bladder 28 may be rolled back over the outer periphery of base 12 so that both sections 34, 36 effectively are withdrawn from the area of the aperture 26 in a direction rearwardly of the base 12. This can be carried out with the bladder 28 preferably partially inflated so as to provide stability to the bladder when rolling the bladder rearwardly of the base 12. The pump 42, as illustrated, may be connected with the base 12 to provide a manipulating device for the entire assembly of base 12, bladder 28 and pump 42 during the procedures that are to be described below.

As illustrated in FIG. 8, with the bladder 28 rolled rearwardly, a distal area 62 of a residual limb 64 to be fitted with a prosthesis socket is fitted with a silicone elastomer suction socket or sleeve 66, for example, a silicon rubber sleeve of the type sold under the name ICEROSS® manufactured by Ossur HF of Reykjavik, Iceland. Such suction sleeves are well known and are marketed by various manufacturers as a cushion liner for prosthetic sockets to be connected to prosthetic devices such as artificial legs and feet. The term "suction socket" connotes that the socket fits over the distal area of a residual limb in an air tight manner so that it does not become separated from the skin of the residual limb.

The suction socket 66 closely conforms to the distal area 62 of residual limb 64 and includes an end fitting 68 to which is attached a tension member 70 which will be described in more detail in connection with the description of FIG. 12 below.

The tension member 70 rigidly interconnects the end fitting 68 of the suction socket 66 with the base 12 via aperture 26 and releasable tension member connector 24.

A moldable and settable socket material 72 includes, in accordance with a preferred embodiment of the invention, but which may be omitted, if desired, a prosthesis device coupler 74 located at its distal end area. The prosthesis socket material 72 preferably is a pre-formed, uncured matrix of reinforcement and settable material, preferably water-cured settable material, that may be provided in rolled up form and which may be unfurled or donned over the residual limb distal area 62 in substantially the same manner as the suction sleeve or socket 66. The prosthesis socket material 72 with or without a prosthesis coupler 74 may be rolled up over the suction socket 66 with the tension member 70 extending through the distal end area of the prosthesis socket material 72 and, optionally, prosthesis device coupler 74.

Thus, the rolled back bladder 28 provides access to the forward side of the base 12 at least in the area thereof that receives the tension member 70 so that the residual limb distal area 64, suction socket 66, uncured prosthesis socket material 72 and, optionally, prosthesis coupler 74 may be located so as to occupy the casting area 38 when the bladder 28 is folded or rolled back over the base 12 to assume its forward, casting position as illustrated in FIGS. 9 and 10.

As shown in FIG. 9, bladder 28 is in process of being rolled forwardly relatively to the base 12 with the bladder 28 partially inflated at a selected pressure that enables convenient rolling of the bladder 28 over the base 12 while enveloping the distal area 62 of residual limb 64 with the suction socket 66 and prosthesis socket material 72 located at a casting position while secured to the base 12 through the tension member 70. The bladder 28 is rolled forwardly as shown in FIG. 10 until it entirely envelops the casting material 72 within a casting area 38 defined by the inner tubular section 34 of the bladder 28. Of course, when enveloping the prosthesis socket material 72 and the residual limb distal area 62 the casting area 38 is distorted into a larger volume than its relaxed volume without the residual limb, suction socket and prosthesis material located in the casting area. Upon pressurization of the bladder 28 to a selectable pressure, for example 10 mm of mercury, the distal area 62 of the residual limb is caused to be compressed circumferentially along with the prosthesis socket material 72 and the suction socket 66, with the result that a reaction force is created between the tension member connector on base 12 and the tension pin 70 whereby the base 12 exerts a tractive force on tension member 70 in a distal direction relative to the residual limb distal area 62, as indicated by arrow 76. However, the base member 12 is connected to the tension member 70 and when urged in a distal direction by the pneumatic pressure in the bladder, applies a tractive force to member 70 that is transmitted to end fitting 68 of suction sleeve 66 in the direction of arrow 76 to cause an axial force to be applied to the suction socket 66 to thereby elongate and tension the distal area 62 of residual limb 64 to cause such distal area to be reduced in diameter and elongated somewhat while under pressure from the inflated bladder 28.

Prior to rolling the bladder 28 over the molding or prosthesis socket material 72, the prosthesis socket material is conditioned to initiate curing of the socket material, preferably by soaking the prosthesis socket material in water or other fluid that is convenient and safe to use in a prosthesis socket casting environment. Thus, while curing, the distal area 62 is compressed by the inflated bladder 28 and a tension reaction load is imposed on the distal area 62 of the residual limb by the reaction force created by inflation of the bladder against the base member 12 which creates a tractive force on member 70 to thereby tension and elongate the distal area 62 of residual limb while the material 72 is undergoing curing under pressure in the casting area from the inflated bladder 28.

Figure 11:
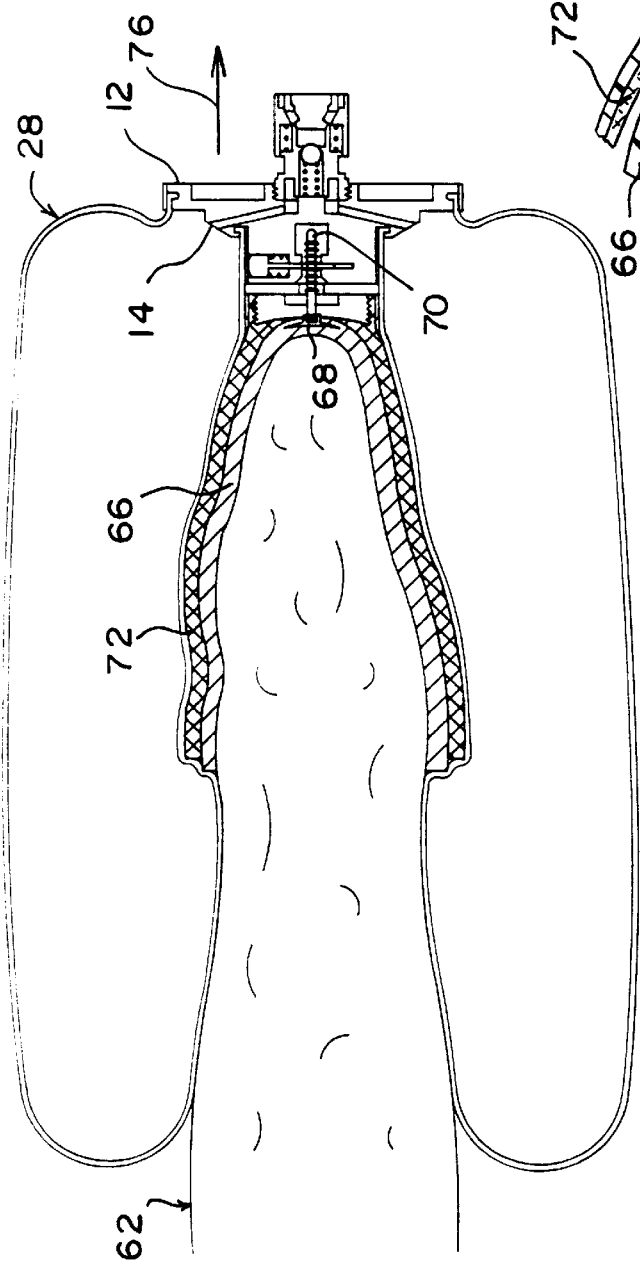
FIG. 11 shows the prosthesis socket casting device of the invention with the bladder in fully inflated condition exerting compression on the residual limb distal area, suction socket and prosthesis material and with a tension force applied to the tension member through the base due to reaction forces resulting from the relationship between the inflated bladder, the residual limb, the suction sleeve and the prosthesis material.

As illustrated in FIG. 11, the pump 42 may be removed from the base 12 during curing of the material 72 over an appropriate period of time required for such curing of the material.

Figure 12:
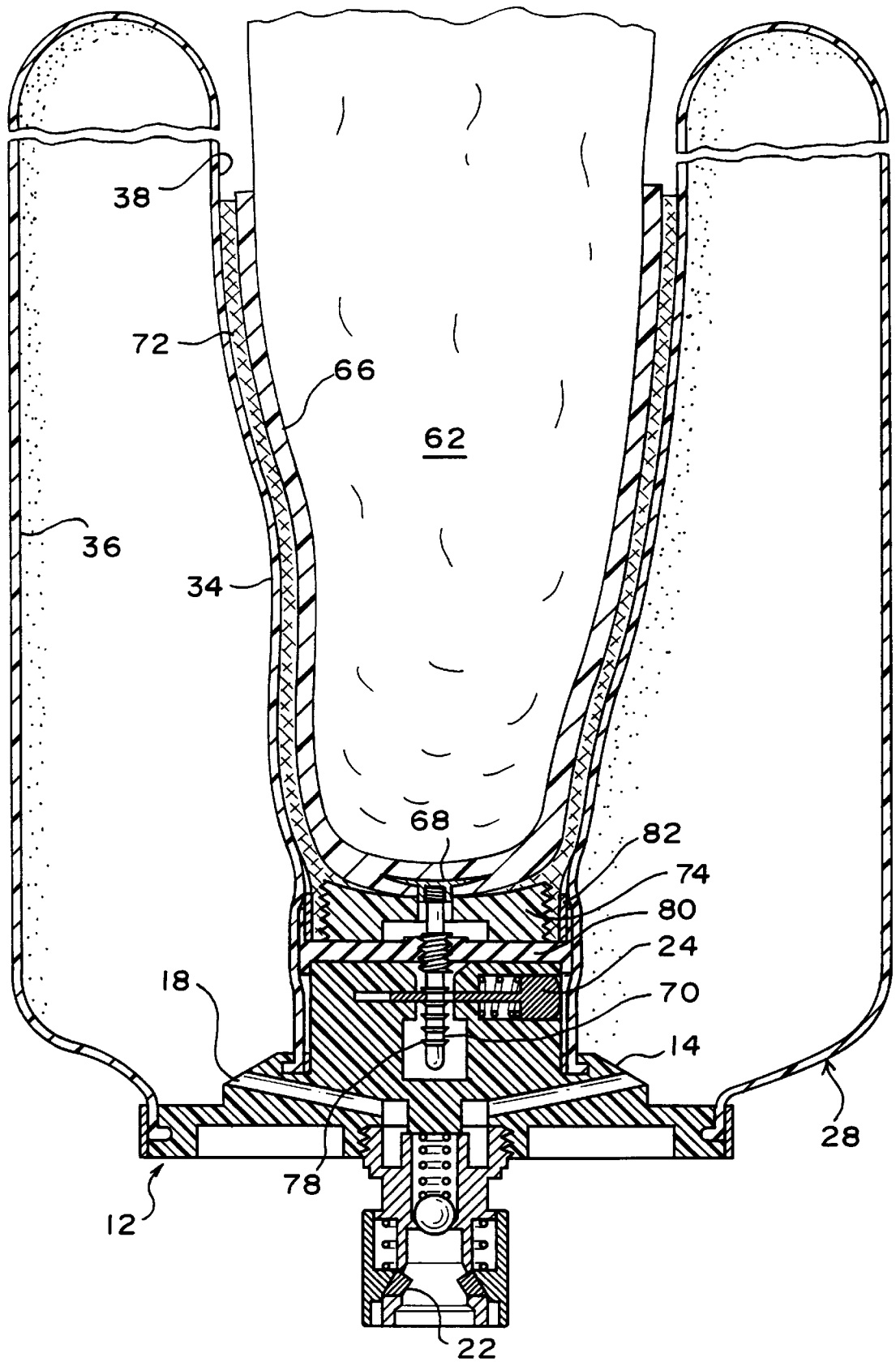
FIG. 12 is a section view showing details of the base, suction sleeve, prosthesis material and prosthesis coupler, tension member and an associated releasable tension member connector carried by the base as well as the molding bladder connection to the base and air conduit/check valve details.

FIG. 12 illustrates a preferred embodiment of the base 12 and associated structure, including the bladder 28 in more detail. The assembly of the suction socket 66, the material 72, the prosthesis device coupler 74, the end fitting 68 and tension pin 70 are described in pending U.S. patent application Ser. No. 08/559,311 filed Nov. 15, 1995, and co-owned by the Assignee of the present invention, which is incorporated herein by reference. Essentially, the suction socket 66 is formed of a highly compliant silicone elastomer that may or may not be reinforced with fabric or filaments to control distention of the suction socket at least in the distal direction while permitting distention of the suction socket in the radial direction. End fitting 68 is molded within the body of the suction socket 66 and includes a threaded fitting for receiving a threaded end of tension member 70 formed as a pin having enlarged ridges or protrusions 78 thereon that interact with releasable tension member connector 24 to permit positive engagement at various positions between the pin 70 and the base 12 as the pin 70 is progressively advanced into the aperture 26 (see FIG. 1) in base 12 when the residual limb distal area 62, suction socket 66, prosthesis material 72 and coupler 74 are advanced into engagement with the forward side 14 of base member 12.

A stabilizer ring 80 may be threaded onto a threaded portion of tension member 70 to center and stabilize the prosthesis coupler 74 relative to the pin 70 and to retain a metal ring 82 that secures the prosthesis socket material 72 to the prosthesis coupler 74 during molding and setting of the prosthesis socket material 72.

The prosthesis device coupler 74 preferably includes outer peripheral ridges or grooves that engage the prosthesis socket material 72 to form a firm union between the coupler 74 and the prosthesis socket material 72 when the socket material is fully cured. The stabilizer ring 80 is removed from the assembly after the tension member 70 has been released from the base 12 following curing of the prosthesis socket material 72.

The prosthesis socket material 72, for example, may comprise any suitable combination of hardenable (curable), moldable compounds and reinforcement materials that will achieve the formation of a definitive socket having physical characteristics necessary or desirable for a prosthesis socket, for example, a definitive socket to be worn with a prosthesis device attached to the prosthesis device coupler 74. A preferred embodiment of a socket preform comprises a porous or web-like compliant tubular braided carbon fiber sleeve available from Atkins & Pierce, 2 Braid Way, Covington, Ky. as product nos. WGM4, WGM5.00 and WGM6.00 (4", 5" and 6", respectively, biaxial carbon fiber sleeves), pre-impregnated with a water curable polyisocyanate type pre-polymer resin 47 available under I.D. No. 41-3701-0524-3 from 3M Company of Minneapolis, Minn. This resin is activatable and rendered moldable by the addition of water to the resin and cures to a hardened condition quite rapidly in a manner typical of such resins.

The specific prosthesis material 72 does not constitute a part of this invention and is described herein for a fuller understanding of the invention. Likewise, the material constituting the suction socket 66 does not constitute a part of this invention per se other than its structural arrangement and function as already described. Clearly, any appropriate suction socket could be utilized as suction socket 66, provided that it closely couples the distal area 62 of a residual limb with a tension member 70 so that, upon tension being applied to tension member 70, axial force will be transmitted to end fitting 68 into the suction socket 66 and then transferred to the distal area 62 of the residual limb to thereby elongate and tension the residual limb distal area while reducing the circumference of the distal area in response to the tension force. Likewise, the prosthesis material 72 may be constituted of any moldable and settable material usable as a definitive prosthesis socket or otherwise as a socket to be associated with a distal area of a residual limb in close fitting relationship. It will be understood that the socket 72 is normally worn over a suction socket 66 during use, so the presence of the socket 66 during molding of the prosthesis socket material 72 results in a properly fitted and contoured prosthesis socket when the material 72 has cured. Pressure relief pads may be incorporated in the prosthesis socket as needed in accordance with known techniques.

The use of the stabilizing ring 80 is optional and the dimensions of the ring 80 may be varied to suit various assemblies of suction socket 66, prosthesis material 72, prosthesis coupler 74 and tension member 70.

As seen in FIG. 12, the tension member connector 24 is accessible from the front side 14 of base member 12 when the bladder 28 is rolled rearwardly relative to the base member 12 to thereby enable release of the tension member 70 following molding and setting of the prosthesis material 72 and at least partial deflation of the bladder 28, as illustrated, for example, in FIG. 7.

Accordingly, operation of the prosthesis socket casting device will be readily comprehensible from the foregoing description. More specifically, to carry out formation or "casting" of a prosthesis socket from a moldable and settable prosthesis material 72, the following procedure may be followed using the apparatus described above. A suction socket 66 is first donned over a distal area 62 of a residual limb 64 with the tension member 70 extending in a distal direction away from the distal area of the residual limb. A moldable and settable material 72 is then placed over the suction socket 66, for example by unfurling or donning a pre-formed prosthesis socket material over the suction socket 66 so that it closely conforms to the outer contour of the suction socket 66 with the tension member 70 extending through and beyond the prosthesis socket material 72. If a prosthesis coupler 74 is provided, the tension member extends freely through the coupler 74. The prosthesis socket material 72 preferably is pre-formed with a coupler 74 and a metal retaining ring 82 as illustrated in FIG. 12.

The stabilizing ring 80 is then threaded onto the tension member 70 to stabilize the position of the tension member 70 relative to the prosthesis coupler 74 and to center the pin 70 in base member 12. The forward side 14 of the base member 12 may include a protrusion that contains the tension member connector 24 and the aperture 26, all as illustrated in FIGS. 1 and 12.

The bladder 28 is rolled rearwardly relative to the base member 12 to a position as shown in FIG. 7 to expose the aperture 26 and the tension member connector 24. Preferably, the bladder 28 is partially inflated to facilitate its manipulation to the position shown in FIG. 7.

Tension member 70 is then inserted into aperture 26 wherein the protrusion thereon engage the tension member connector 24 with the elements arranged as shown in FIG. 8. The bladder 28 is then rolled forwardly relative to the base 12 and the distal area 62 of the residual limb as shown in FIGS. 9 and 10. When fully extended to the forward position as shown in FIG. 10, the bladder 28 is then inflated by hand pump 42 which has been secured to the base 12 as shown in FIG. 10 to enable the supply of pressurized air to the interior of the bladder 28 as illustrated, for example, in FIG. 6. When inflated, the bladder assumes the position as shown in FIGS. 11 and 12 wherein the distal area 62 of residual limb 64 is confined in the casting area 38 along with the suction sleeve 66 and the prosthesis socket material 72. Upon selective inflation of the bladder 28 (for example up to about 10 mm Hg.), the residual limb distal area, suction socket and prosthesis socket material are radially and circumferentially compressed within casting area 38 by the inner section 34 of bladder 28. However, because the volume of the residual limb distal area 62, suction socket 66, and prosthesis socket material 72 is larger than the normal relaxed or empty volume of the casting area 38, and also due to the typical tapered configuration of a residual limb distal area, a net resultant force is produced by inflation of the bladder 28 tending to urge base member 12 rearwardly away from the residual limb distal area due to the force generated by the pneumatic pressure within bladder 28. This resultant force is transmitted to tension member 70 in general proportion to the pressure within bladder 28 and the force in turn is transmitted as a tractive force to the end fitting 68 and the suction socket 66. The tractive force exerted on the distal end of socket 66 is transmitted to the distal area 62 of the residual limb to thereby cause distention, elongation and reduction in diameter of the distal area 62 of the residual limb in a distal direction while, at the same time, the pressure within bladder 28 radially and circumferentially compresses the distal area of the residual limb with the prosthesis socket material 72 confined between the inner section 34 of the bladder 28 and the suction socket 66.

The net result of the compression and tension loading applied to the distal area 62 of the residual limb, prosthesis socket material and the suction socket 66 results in a close-fitting and precisely configured prosthesis socket formed of the now cured and set prosthesis socket material 72.

Release of the tension member 70 by manipulation of the tension member connector 24 permits separation of the base member 12 and the bladder 28 from the residual limb distal area, suction socket and prosthesis socket formed of the hardened socket material. The tension pin is then released from ring 80 and the end fitting 68 and the prosthesis socket is separated from the suction socket 66 in a known manner. The hardened prosthesis socket material 72 then may be finally trimmed to the extent needed to provide a comfortable prosthesis socket that is in substantially finished form when it is released from the suction socket 66 and the residual limb distal area 62. A prosthesis device, if desired, may then be connected to the prosthesis coupler 74 in a known, conventional manner.

Deflation of the bladder 28, of course, may be carried out by using the pressure release valve 58 associated with pump 42 or by other suitable means that may be readily adapted by a person skilled in the art.

It will be noted that a completely self-contained prosthesis socket casting device is provided by the apparatus described herein, which is used typically by simply mounting it to the distal area of a residual limb without any other support or tractive force generating implement. The tractive force exerted on the tension member 70 in the embodiment described above is created by the casting device itself as a result of forces generated during the casting procedure.

Figure 14:
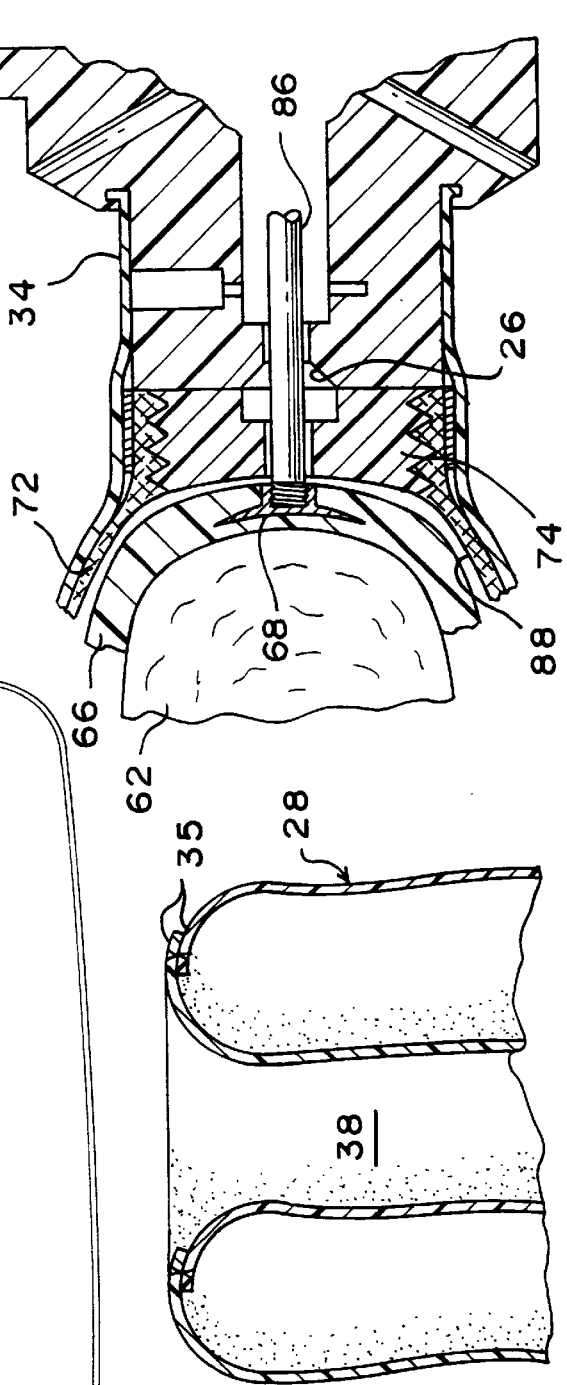
FIG. 14 shows an alternate form of the suction socket connector and base member.

For some applications, it may be desirable to omit the tension member connector 24 in base member 12 so that the bladder 28 can be utilized simply as a compression device during molding of a moldable, settable molding or prosthesis sleeve material 72 without reacting tension load into a tension member 70. For example, in the event that a simple plaster of paris prosthesis mold sleeve or the like is to be formed using the described prosthesis casting or molding apparatus and process, an arrangement such as illustrated in FIG. 14 could be utilized, wherein the base member 12 does not include a tension member connector and instead a centering or guide pin 86 extending through base member aperture 26 in a centered and stabilized manner could be utilized with or without the application of separate tension force or preload applied to the pin 86 by some external source from a position outside the rearward face of base member 12. Appropriate air passages and sealing devices for the air passages, of course, would be provided to maintain the pressure within the bladder 28 following its inflation, as described previously. When using this arrangement of casting device, a space or gap 88 could be provided between the distal end of the suction socket 66 and the adjacent surface or side of the prosthesis coupler 74 or the forward side of the base member 12 in the event that a coupler 74 is not utilized. The space 88 would permit the distal area 62 of the residual limb to expand somewhat in a distal direction during compression of the prosthesis material 72 by the inflated bladder 28. In using the embodiment illustrated in FIG. 14, air pressure in the bladder 28 would be carefully regulated so as to control the distal displacement of the base member 12 by the air pressure in the bladder. However, it will be noted that pin 86 extends freely through the base member 12 so that the base member 12 is free to move somewhat in a distal direction relative to the suction socket 66 when the bladder 28 is inflated.

The specific embodiments of the invention described herein are intended to be illustrative only and various modifications thereto may be envisioned and implemented by a person skilled in the art without departing from the spirit and scope of the invention which is defined in the claims that follow.

What is claimed is:

1. A prosthetic socket casting device comprising:
   a base having a forward side;
   an elongated annular molding bladder carried by the base, the bladder peripherally enclosing a generally centrally located casting area when inflated and extended from the forward side of the base, the bladder further comprising a pliable, air-impermeable, relatively non-stretchable sheet material enclosing, in cooperation with the base, an air chamber peripherally surrounding the casting area;
   said casting area including an open residual limb receiving end and extending from said end to the base; and
   an air passage enabling controlled supply of pressurized air to the air chamber.

2. A prosthetic socket casting device according to claim 1, said bladder comprising:
   a continuous tubular member having opposed ends and extending between said opposed ends with one portion thereof folded inside out over the remaining portion thereof;
   said opposed ends sealingly secured to said base;
   said air chamber located between the folded layers of the tubular member.

3. A prosthetic socket casting device according to claim 1, said bladder comprising:
   an inner tube section having opposed ends and sealingly secured at one end to the base;
   an outer tube section having opposed ends and extending over the inner tube section in spaced relationship therewith, said outer tube section also sealingly secured at one end to said base;
   said inner and outer tube sections sealingly joined at their opposed ends located opposite said base;
   said air chamber defined by the space between the inner and outer tube sections;
   the one outer tube end being secured to said base substantially concentrically relative to the one inner tube end.

4. A prosthetic socket casting device according to claim 2, said opposed ends secured substantially concentrically to the forward side of the base.

5. A prosthetic socket casting device according to claim 2, said continuous tubular member being rollable continuously over the base member in a rearward direction opposite the base forward side so as to envelope the base member at one position at least.

6. A prosthetic socket casting device according to claim 1, including a releasable tension member connector carried by the base.

7. A prosthetic socket casting device according to claim 4, including a releasable tension member connector carried by the base; said tension member connector located within the inner tube end.

8. A prosthetic socket casting device according to claim 7, including a release mechanism for the tension connector member located on the base within the inner tube end.

9. A prosthetic socket casting device according to claim 1, including a tension member connector disposed on the forward side of the base at a position accessible from said casting area.

10. A prosthetic socket casting device according to claim 1, said air passage comprising an air passage in the base in communication with the air chamber; and a valve in the air passage arranged to control flow of air through the passage.

11. A prosthetic socket casting device according to claim 10, said air valve comprising a normally closed check valve preventing egress of air from the air chamber when closed, but openable for permitting air to pass through the air passage in either direction.

12. A prosthetic socket casting device according to claim 10, said air passage including an air passage quick engage/release coupling arranged to receive a pump quick engage/release fitting.

13. A prosthetic socket casting device according to claim 12, said valve comprising a normally closed check valve and a biasing device for biasing the check valve towards a closed position.

14. A prosthetic socket casting device according to claim 13, including an air pump including a pump quick engage/release fitting configured to cooperate with and to be received by the air passage coupling;
    said pump fitting including an air valve opener arranged to open the check valve when the pump fitting and air passage coupling are engaged together.

15. A prosthetic socket casting device according to claim 14, said pump including a manual air displacer movable to cause pressurized air flow out through the pump fitting when moved; and a pressure gauge for indicating static air pressure in the air supply conduit and said bladder when the check valve is open and the air passage coupling is engaged with the pump fitting.

16. A prosthetic socket casting device comprising:
    a base having a forward side;
    an elongated annular molding bladder carried by the base, the bladder peripherally enclosing a generally centrally located casting area and extendable when inflated and extended from the forward side of the base, the bladder further comprising a pliable, air-impermeable, relatively non-stretchable sheet material enclosing, in cooperation with the base, an air chamber peripherally surrounding the casting area;
    said casting area including an open residual limb receiving end and extendable to the base;
    an air passage enabling controlled supply of pressurized air to the air chamber;
    a residual limb suction socket disposed in said casting area, said suction socket arranged to receive a residual limb distal area and including a closed end located adjacent said base;

a moldable and settable molding material positioned over the suction socket between the suction socket and the bladder;

said casting area when empty and when the bladder is inflated to fully extend the bladder being smaller in volume than the volume of said suction socket fitted to a residual limb distal area and said molding material.

17. A prosthetic socket casting device according to claim 16, said bladder comprising a continuous tubular member having opposed ends and extending between said opposed ends with one portion thereof folded inside out over the remaining portion thereof; said opposed ends sealingly secured to said base; said air chamber located between the folded layers of the tubular member.

18. A prosthetic socket casting device according to claim 17, said opposed ends secured substantially concentrically to the forward side of the base.

19. A prosthetic socket casting device according to claim 18, including a releasable tension member connector on the base and a release mechanism for the tension member connector located on the base within the inner tube end.

20. A prosthetic socket casting device according to claim 16, including a releasable tension member connector carried by the base; a tension member secured to the suction socket closed end; said tension member extending towards and engaging said tension member connector so that the suction socket end is releasably coupled to said base by said tension member; said tension member connector disposed on the forward side of the base at a position accessible from said casting area.

21. A prosthetic socket casting device according to claim 16, said air passage comprising an air passage in the base in communication with the air chamber; and a valve in the air passage arranged to control flow of air through the passage, said air valve comprising a normally closed check valve preventing egress of air from the air chamber when closed, but openable for permitting air to pass through the air passage in either direction.

22. A prosthetic socket casting device according to claim 16, said air passage comprising an air passage in the base in communication with the air chamber; and a valve in the air passage arranged to control flow of air through the passage, said air passage including an air passage quick engage/release coupling arranged to receive a pump quick engage/release fitting;

said valve comprising a normally closed check valve and a biasing device for biasing the check valve towards a closed position;

an air pump including a pump quick engage/release fitting configured to cooperate with and to be received by the air passage coupling;

said pump fitting including an air valve opener arranged to open the check valve when the pump fitting and air passage coupling are engaged together;

said pump including a manual air displacer movable to cause pressurized air flow out through the pump fitting when moved and a pressure gauge for indicating static air pressure in the air supply conduit and said bladder when the check valve is open and the air passage coupling is engaged with the air pump fitting.

23. A prosthetic socket casting device according to claim 20, including a tension indicator for indicating tensile force between said tension member and said tension member connector when said bladder is inflated to exert a compressive force on said prosthesis socket material and a suction socket containing a residual limb distal area located in said casting area.

24. A prosthetic socket casting device according to claim 16, including a releasable tension member connector carried by the base; a tension member secured to the suction socket closed end; said tension member extending towards and engaging said tension member connector so that the suction socket end is releasably coupled to said base by said tension member; and including a prosthesis coupler attached to the socket material, the prosthesis coupler located adjacent said suction socket closed end between said suction socket end and said base; said coupler including an opening extending therethrough; said tension member extending through said opening in said coupler with the coupler located between the suction socket closed end and said tension member connector.

25. A method of casting a prosthetic device on a residual limb distal area comprising:

donning a suction socket including a tension member at a closed distal end thereof over the distal area of a residual limb with the tension member extending outwardly in a distal direction;

placing a moldable and settable uncured prosthetic device material over and in close conformity with the suction socket and so that the tension member extends in a distal direction through the prosthetic device material;

mounting an annular, inflatable bladder comprising a relatively inextensible pliable material on a base member to produce a generally central open casting area extending from a forward side of the base member towards a residual limb receiving central opening spaced from the base member when the bladder is inflated and positioned to extend from the base member in a forward direction, the bladder being movable by a rolling action of the bladder relative to the base member in forward and rearward directions;

rolling the bladder back from the forward side of the base member to provide access to the casting area by the residual limb distal area, suction socket and prosthetic device material and access to the base member by the tension member;

coupling the tension member to the forward side of the base member to restrain relative movement in the distal direction between the tension member and the base member while placing the residual limb distal area, suction socket and prosthetic device material in the casting area;

rolling the bladder forward relative to the base member to a position whereat it extends forwardly of the base member and envelops the residual limb distal area, suction socket and prosthetic device material in the casting area while the tension member is connected to the base member;

inflating the bladder to a selected pressure to cause the bladder material to extend inwardly towards the casting area to compress the residual limb distal area, suction socket and prosthetic device material and to cause a reaction force between the tension member and base member causing the base member to exert a tractive force on the tension member when the bladder is selectively inflated at such forward position;

maintaining the residual limb distal area, suction socket and prosthetic device material under compression and the tension member under tension from the tractive force while curing the prosthetic device material;

releasing air pressure from the bladder, releasing the tension member and separating the residual limb distal area, suction socket and cured prosthetic device material from the bladder and the base member.

26. The method according to claim 25, including carrying out the step of inflating the bladder by delivering a selectable inflating air pressure through an air passage in the base member to an air chamber of the bladder.

27. The method according to claim 25, including using as the bladder a single-piece tubular element partially folded inside out over itself to form inner and outer tubular sections having a pair of free ends sealingly connected to the base member with the space between the tubular sections defining an inflatable air chamber and the space within the inner tubular section defining the casting area, and carrying out the step of rolling the bladder back from the forward side of the base member by rolling both tubular sections together relative to the base member in a direction rearwardly of the base member to provide access of the tension member to the forward side of the base member.

28. The method according to claim 25, including providing a prosthesis device coupler on the distal area of the prosthetic device material; extending the tension member freely through the prosthesis device coupler when coupling the tension member to the base member with the prosthesis device coupler disposed between the closed distal end of the suction socket and the base member, and permanently joining together the prosthesis device coupler and the prosthetic device material during curing of the prosthetic device material.

29. A method of casting a prosthetic device on a residual limb distal area comprising:
   placing a moldable and settable uncured prosthetic device material over and in close conformity with a distal area of a residual limb;
   mounting an annular, inflatable bladder comprising a relatively inextensible pliable material on a base member to produce a central open casting area extending from a forward side of the base member towards a residual limb receiving central opening spaced from the base member when the bladder is inflated and positioned to extend from the base member in a forward direction, the bladder being movable by a rolling action of the bladder relative to the base member in forward and rearward directions;
   rolling the bladder back from the forward side of the base member to provide access to the casting area by the residual limb distal area and prosthetic device material;
   placing the residual limb distal area with the prosthetic device material in the casting area adjacent the base member;
   rolling the bladder forward relative to the base member to a position whereat it extends forwardly of the base member and envelops the residual limb distal area and prosthetic device material in the casting area;
   inflating the bladder to a selected pressure to cause the bladder material to extend inwardly towards the casting area to compress the residual limb distal area and prosthetic device material;
   maintaining the residual limb distal area and prosthetic device material under compression while curing the prosthetic device material;
   releasing air pressure from the bladder and separating the residual limb distal area and cured prosthetic device material from the bladder and the base member.

30. The method according to claim 29, including rolling the bladder rearward relative to the base member when carrying out the step of separating the residual limb distal area and cured prosthetic device material from the bladder and the base member.

31. The method according to claim 29, including carrying out the step of inflating the bladder by delivering a selectable inflating air pressure through an air passage in the base member to an air chamber of the bladder.

32. The method according to claim 29, including using as the bladder a single piece tubular element partially folded inside out over itself to form inner and outer tubular sections having a pair of free ends sealingly connected to the base member with the space between the tubular sections defining an inflatable air chamber and the space within the inner tubular section defining the casting area, and carrying out the step of rolling the bladder back from a forward side of the base member by rolling both tubular sections together relative to the base member in a direction rearwardly of the base member to provide access of the residual limb distal area and prosthetic device material to the forward side of the base member.

33. The method according to claim 32, including donning a suction socket over the distal area of the residual limb distal area prior to placing a moldable and settable uncured prosthetic device material over the distal area; and carrying out the curing of the prosthetic device material under compression from the inflated bladder while the prosthetic device material is maintained in close conformity with the distal area of the residual limb and the suction socket.

34. A prosthetic socket casting device for casting a socket corresponding to a residual limb distal end, comprising:
   a suction prosthetic socket including an end fitting at a distal end of the socket;
   a tension member connected to the end fitting;
   a tension member connector device including structure capable of engaging and releasably retaining against withdrawal said tension member when said tension member is coupled to said connector device;
   an elongated annular molding bladder, including inner and outer walls connected to the tension member in a manner to react tension force in the distal direction between the tension member and the bladder when the bladder is inflated over a generally central casting area containing a residual limb distal end over which said suction prosthetic socket has been donned, said generally central casting area defined by the inner wall of said bladder, the inner and outer walls of said bladder further being formed of a pliable, air-impermeable, relatively non-stretchable sheet material defining an air chamber between the inner and outer walls peripherally surrounding the casting area;
   said casting area including an open end for receiving a suction socket and said tension member; and
   an air passage arrangement enabling controlled supply of pressurized air to the air chamber.

35. The prosthetic socket casting device as claimed in claim 34, said bladder comprising a tubular member rollable continuously over the tension member connector towards and away from a suction socket located in the casting area.

36. A prosthetic socket casting device according to claim 34, including a tension member connector releasing device carried by the tension member connector device.

37. A prosthetic socket casting device according to claim 34, including a moldable and settable prosthetic device molding material configured to fit between a suction socket inserted in the casting area and the bladder.

38. A method of casting a prosthetic device corresponding to a residual limb distal area, comprising:
   donning a suction socket including a tension member at a closed distal end thereof over a member corresponding to a residual limb distal area with the tension member extending in a distal direction;

connecting the tension member to a tension member connector device that releasably engages and retains the tension member against withdrawal;

placing a moldable and settable uncured prosthetic device material over and in close conformity with the donned suction socket with the tension member extending distally beyond the prosthetic device material;

placing an annular, inflatable bladder including inner and outer walls defining an air chamber and formed of a relatively inextensible pliable material and defining a generally central casting area within the inner wall having a minimum volume when the air chamber is inflated that is less than the volume of a donned suction socket over the prosthetic device casting material and donned suction socket, and further with the bladder engaging the tension member connector device so as to enable reaction of tension force in the distal direction between the tension member and the bladder;

inflating the air chamber to reduce the volume of the casting area to cause compression of the prosthetic device casting material over the donned suction socket and to cause tension loading of the tension member by resultant reaction forces created between the bladder and the donned suction sleeve via the tension member in a distal direction when the bladder is inflated;

curing the prosthetic socket material while the socket material is compressed and while the underlying donned socket material is tensioned by said reaction forces;

deflating the air chamber and removing it from the cured prosthetic socket material;

separating the cured prosthetic socket material from the suction socket.

* * * * *